(12) United States Patent
Asari et al.

(10) Patent No.: US 9,724,309 B2
(45) Date of Patent: Aug. 8, 2017

(54) FILM-FORM PREPARATION AND METHOD FOR PRODUCING THE SAME

(75) Inventors: Daisuke Asari, Ibaraki (JP); Mitsuhiko Hori, Ibaraki (JP); Takuya Shishido, Ibaraki (JP)

(73) Assignee: NITTO DENKO CORPORATION, Osaka (JP)

(*) Notice: Subject to any disclaimer, the term of this patent is extended or adjusted under 35 U.S.C. 154(b) by 0 days.

(21) Appl. No.: 13/073,022

(22) Filed: Mar. 28, 2011

(65) Prior Publication Data
US 2011/0243997 A1    Oct. 6, 2011

(30) Foreign Application Priority Data

Mar. 30, 2010   (JP) .................... 2010-079430

(51) Int. Cl.
*A61K 8/02*   (2006.01)
*A61K 9/70*   (2006.01)
*A61K 9/00*   (2006.01)

(52) U.S. Cl.
CPC .......... *A61K 9/7007* (2013.01); *A61K 8/0241* (2013.01); *A61K 9/0056* (2013.01)

(58) Field of Classification Search
CPC .................................................. A61K 8/0241
USPC ...................................................... 424/443
See application file for complete search history.

(56) References Cited

U.S. PATENT DOCUMENTS

| | | | |
|---|---|---|---|
| 4,292,426 A * | 9/1981 | Orii et al. ............. | 536/95 |
| 4,639,368 A | 1/1987 | Niazi et al. | |
| 4,687,660 A | 8/1987 | Baker et al. | |
| 5,641,637 A * | 6/1997 | Hudak et al. ......... | 435/7.24 |
| 5,948,430 A | 9/1999 | Zerbe et al. | |
| 6,156,343 A | 12/2000 | Morita et al. | |
| 6,455,053 B1 | 9/2002 | Okada et al. | |
| 6,531,151 B1 | 3/2003 | Besse | |
| 6,649,186 B1 | 11/2003 | Robinson et al. | |
| 2001/0006677 A1 | 7/2001 | McGinity et al. | |
| 2003/0099690 A1 | 5/2003 | Awamura et al. | |
| 2005/0008735 A1 | 1/2005 | Pearce | |
| 2005/0079138 A1 | 4/2005 | Chickering et al. | |
| 2005/0147653 A1 | 7/2005 | Yasuda et al. | |
| 2005/0163830 A1 | 7/2005 | Rademacher et al. | |
| 2005/0175675 A1 | 8/2005 | Sceibertz | |
| 2005/0186257 A1 | 8/2005 | Manegold et al. | |

(Continued)

FOREIGN PATENT DOCUMENTS

CA   1067407 A   12/1979
CA   2 339 836 A1   3/2000

(Continued)

OTHER PUBLICATIONS

Nasirov et al., Anabasine hydrochloride—A New Antismoking agent, Neew Drugs, 1978, pp. 281-283.*

(Continued)

*Primary Examiner* — Benjamin Packard
(74) *Attorney, Agent, or Firm* — Sughrue Mion, PLLC

(57) ABSTRACT

The present invention provides a film-form preparation having a rapid dissolution profile in the mouth and sufficient film strength, and also having excellent appearance and feel. More specifically, the present invention provides a film-form preparation including: a water-soluble and a polar organic solvent-soluble edible polymer; and polar organic solvent-insoluble drug particles.

8 Claims, 10 Drawing Sheets

(56) References Cited

U.S. PATENT DOCUMENTS

| | | | |
|---|---|---|---|
| 2005/0208110 A1* | 9/2005 | Singh et al. | 424/443 |
| 2006/0052340 A1 | 3/2006 | Tsuzuki et al. | |
| 2006/0057207 A1 | 3/2006 | Ziegler et al. | |
| 2006/0078597 A1 | 4/2006 | Jentzsch et al. | |
| 2007/0098790 A1* | 5/2007 | Jiang | 424/468 |
| 2007/0122455 A1 | 5/2007 | Myers et al. | |
| 2007/0178055 A1* | 8/2007 | Buch et al. | 424/53 |
| 2007/0237871 A1 | 10/2007 | Furusawa | |
| 2007/0281003 A1* | 12/2007 | Fuisz et al. | 424/443 |
| 2007/0298105 A1 | 12/2007 | Hwang | |
| 2008/0003267 A1 | 1/2008 | Spencer et al. | |
| 2008/0200452 A1 | 8/2008 | Obermeier et al. | |
| 2009/0155351 A1 | 6/2009 | Hejl et al. | |
| 2009/0196908 A1 | 8/2009 | Lee et al. | |
| 2009/0317531 A1 | 12/2009 | Reh et al. | |
| 2010/0150986 A1* | 6/2010 | Nagaso et al. | 424/439 |
| 2011/0054043 A1* | 3/2011 | Funaki et al. | 514/772.4 |
| 2011/0111037 A1 | 5/2011 | Boit et al. | |
| 2011/0182993 A1 | 7/2011 | Asari et al. | |
| 2011/0293673 A1 | 12/2011 | Asari et al. | |
| 2011/0293720 A1 | 12/2011 | General et al. | |
| 2011/0300216 A1 | 12/2011 | First et al. | |
| 2011/0305768 A1 | 12/2011 | Mao et al. | |

FOREIGN PATENT DOCUMENTS

| | | |
|---|---|---|
| CA | 2615533 A1 | 1/2007 |
| CN | 1638748 A | 7/2005 |
| CN | 1652824 A | 8/2005 |
| CN | 1658835 A | 8/2005 |
| CN | 1758927 A | 4/2006 |
| CN | 101287445 A * | 10/2008 |
| CN | 102300565 A | 12/2011 |
| EP | 1522225 A1 | 4/2005 |
| EP | 1 752 127 A1 | 2/2007 |
| FR | 2933299 A1 | 1/2010 |
| JP | 51-29218 A | 3/1976 |
| JP | 7-187993 A | 7/1995 |
| JP | 10-179045 A | 7/1998 |
| JP | 11-116465 A | 4/1999 |
| JP | 11-116469 A | 4/1999 |
| JP | 2001-504106 A | 3/2001 |
| JP | 2001-288074 A | 10/2001 |
| JP | 2001-318348 | 11/2001 |
| JP | 2002-523359 T | 7/2002 |
| JP | 2004-043450 A | 2/2004 |
| JP | 3496727 B2 | 2/2004 |
| JP | 2005-008568 | 1/2005 |
| JP | 2005-21124 A | 1/2005 |
| JP | 2005060244 A * | 3/2005 |
| JP | 2005-511522 A | 4/2005 |
| JP | 2005-517722 A | 6/2005 |
| JP | 2005-342154 A | 12/2005 |
| JP | 2005-536443 A | 12/2005 |
| JP | 2005-537233 A | 12/2005 |
| JP | 2006-513269 | 4/2006 |
| JP | 2007-500252 | 1/2007 |
| JP | 2007-509172 A | 4/2007 |
| JP | 2007-528876 T | 10/2007 |
| JP | 2008-517935 A | 5/2008 |
| JP | 2008-169138 A | 7/2008 |
| JP | 2009-507854 | 2/2009 |
| JP | 2009-510136 | 3/2009 |
| JP | 2010-158173 A | 7/2010 |
| JP | 2010-172256 A | 8/2010 |
| JP | 2010-209104 A | 9/2010 |
| JP | 4597662 B2 | 12/2010 |
| JP | 2011-153113 A | 8/2011 |
| RU | 2 316 316 C2 | 6/2005 |
| RU | 2256442 C2 | 7/2005 |
| WO | 98/20862 A1 | 5/1998 |
| WO | 01/70194 A1 | 9/2001 |
| WO | 03/030882 A1 | 4/2003 |
| WO | 03/030883 A1 | 4/2003 |
| WO | 03/070227 A1 | 8/2003 |
| WO | 03/101420 A1 | 12/2003 |
| WO | 2004/047794 A2 | 6/2004 |
| WO | 2004/066986 A1 | 8/2004 |
| WO | 2004/080499 A1 | 9/2004 |
| WO | 2005039499 A2 | 5/2005 |
| WO | 2005/082048 A2 | 9/2005 |
| WO | 2006/031209 A1 | 3/2006 |
| WO | 2006/047365 A1 | 5/2006 |
| WO | 2006/114604 A2 | 11/2006 |
| WO | 2007009801 A2 | 1/2007 |
| WO | 2007/030754 A2 | 3/2007 |
| WO | 2007/038926 A1 | 4/2007 |
| WO | 2008/089151 A2 | 7/2008 |
| WO | WO 2008149440 A1 * | 12/2008 |
| WO | 2009/099830 A2 | 8/2009 |
| WO | WO 2009128433 A1 * | 10/2009 |
| WO | 2010/015713 A1 | 2/2010 |
| WO | 2010/086989 A1 | 8/2010 |
| WO | 2010/144817 A1 | 12/2010 |

OTHER PUBLICATIONS

Kollidon, BASF, 1998, pp. 35-36.*
ToxNet (http://toxnet.nlm.nih.gov/cgi-bin/sis/search/a?dbs+hsdb:@term+@DOCNO+783, accessed Aug. 17, 2013).*
European Search Report dated Jun. 29, 2011, issued in Application No. 11002555.8.
European Office Action dated May 10, 2012 issued in European Patent Application No. 11002555.8.
The United States Pharmacopeia USP 24. The National Formulary NF 19, Jan. 1, 1999, p. 10 (XP55026035).
First Notification of Office Action issued by The State Intellectual Property Office of China in counterpart CN Application No. 201110078800.1, dated Apr. 1, 2013.
Journal of Nanjing College of Traditional Chinese Medicine, 1984, No. 4, pp. 53-55.
Second Notification of Office Action issued by The State Intellectual Property Office of China in counterpart CN Application No. 201110078800.1, dated Nov. 13, 2013.
Decision of Refusal issued by The State Intellectual Property Office of China in counterpart CN Application No. 201110078800.1, dated Nov. 3, 2014.
Office Action dated May 22, 2014, issued by the State Intellectual Property Office of China in corresponding Chinese Application No. 201110078800.1.
Office Action dated Aug. 26, 2014, issued by the Japanese Patent Office in corresponding Application No. 2011-049504.
Office Action dated Mar. 19, 2015, issued by the Russian Patent Office in counterpart Application No. 2011111666/15.
Decision of Refusal dated Jan. 13, 2015, issued by the Japanese Patent Office in counterpart Japanese application No. 2011-049504.
Office Action dated Mar. 10, 2015. Issued by the Canadian Intellectual Property Office in Canadian Application No. 2750617, which corresponds to U.S. Appl. No. 13/146,829.
Office Action dated Aug. 27, 2013. Issued by the Japanese Patent Office in Application No. 2010548356, which corresponds to U.S. Appl. No. 13/146,829.
Office Action dated Feb. 12, 2014, issued by the Japanese Patent Office in Application No. 2010548356, which corresponds to U.S. Appl. No. 13/146,829.
Third Party Observation issued in JP Application No. 2010548356 notified on Dec. 24, 2013, which corresponds to U.S. Appl. No. 13/146,829.
Fourth Notification of Office Action issued by The State Intellectual Property Office of China in CN Application No. 200980155744.8 dated Oct. 11, 2013, which corresponds to U.S. Appl. No. 13/146,829.
Supplementary European Search Report issued in EP Application No. 09839222.8 dated Jul. 26, 2013, which corresponds to U.S. Appl. No. 13/146,829.
Third Notification of Office Action issued by the State Intellectual Property Office of China in CN Application No. 200980155744.8 dated Apr. 1, 2013, which corresponds to U.S. Appl. No. 13/146,829.

(56) References Cited

OTHER PUBLICATIONS

Office Action issued by the State Intellectual Property Office of China in CN Application 200980155744.8 dated Dec. 12, 2012, which corresponds to U.S. Appl. No. 13/146,829.
Russian Office Action issued in Application No. 2011135837 dated Oct. 19, 2011, which corresponds to U.S. Appl. No. 13/146,829.
Chinese Office Action issued in Application No. 200980155744.8 dated Mar. 22, 2012, which corresponds to U.S. Appl. No. 13/146,829.
International Search report for PCT/JP2009/054335 dated Mar. 31, 2009, which corresponds to U.S. Appl. No. 13/146,829.
European Office Action issued in Application No. 11000618.6 dated Nov. 2, 2012, which corresponds to U.S. Appl. No. 13/014,245.
Extended European Search Report for European Application No. 11000618.6 dated Apr. 20, 2011, which corresponds to U.S. Appl. No. 13/014,245.
Developing Solid Oral Dosage Forms: Pharmaceutical Theory & Practice (edited by Qiu et al, Elvisar, 2009).
Japanese Office Action issued in JP Application No. 2010-079429, and dispatched on Dec. 17, 2013, which corresponds to U.S. Appl. No. 13/072,972.
First Notification of Office Action issued by The State Intellectual Property Office of China in CN Application No. 201110078784.6, dated May 23, 2013, which corresponds to U.S. Appl. No. 13/072,972.
Stankovic, Ivan, Pullulan Chemical and Technical Assessment, Clinical and Technical Assessment 65$^{th}$ JECFA, 2002, pp. 1-8.
Perfetti et al., Influence of Polymer Coating on Strength of Particles: Polymer and Environmental Parameters, BioPowders Mini-Conference-Budapest, 2007, pp. 76-87.
Lliana et al., Diclofenac Solubility: Independent Determination of the Intrinsic Solubility of Three Crystal Forms, J. Med. Chem., 2007, 50, pp. 979-983.
Extended European Search Report issued for EP Application No. 11002556.6, dated Jul. 4, 2011, which corresponds to U.S. Appl. No. 13/072,972.
Russian Office Action issued in Application No. 2011111665 dated Mar. 28, 2011, which corresponds to U.S. Appl. No. 13/072,972.
Office Action dated Apr. 21, 2015, from the Japanese Patent Office in Application No. 2012-003625, which corresponds to U.S. Appl. No. 13/737,255.
European Search Report issued in counterpart EP Application No. 13000089.6 dated Jul. 12, 2013, which corresponds to U.S. Appl. No. 13/737,255.
Communication dated May 21, 2013, issued by the State Intellectual Property Office of the People's Republic of China in Application No. 201110030217.3, which corresponds to U.S. Appl. No. 13/014,245.
Communication dated Jan. 17, 2014, issued by the State Intellectual Property Office of the People's Republic of China in Application No. 201110030217.3, which corresponds to U.S. Appl. No. 13/014,245.
Communication dated Aug. 11, 2014, issued by the State Intellectual Property Office of the People's Republic of China in Application No. 201110030217.3, which corresponds to U.S. Appl. No. 13/014,245.
Communication dated Jan. 23, 2014, issued by the State Intellectual Property Office of the People's Republic of China in Application No. 201110078784.6, which corresponds to U.S. Appl. No. 13/072,972.
Russian Office Action issued in Application No. 2011135837, dated Sep. 19, 2012, which corresponds to U.S. Appl. No. 13/146,829.
Non-Final Office Action dated Jan. 5, 2016 from the United States Patent and Trademark Office issued in U.S. Appl. No. 13/737,255.
Notification of Reexamination dated Mar. 31, 2016 from the State Intellectual Property Office of the P.R.C. issued in corresponding Application No. 201110078800.1.
Yakuzaigaku, Pharmaceutics, ISBN 7-117-00026-0, Apr. 1996, pp. 236-238, 4 pages total.
First Notification of Office Action dated Mar. 24, 2016, issued by the State Intellectual Property Office of China in CN Application No.: 201310007094.0 dated Mar. 24, 2016.
Final Office Action dated Aug. 8, 2016, issued by the U.S. Appl. No. 13/737,255.
Reexamination Decision dated Sep. 18, 2016 from the State Intellectual Property Office of the P.R.C. in counterpart Application No. 201110078800.1.
Communication dated Feb. 20, 2017, issued by the Canadian Patent Office in counterpart Canadian Application No. 2,735,592.
Second Notification of Office Action dated Oct. 19, 2016, from the State Intellectual Property Office of People's Republic of China in Application No. 201310007094.0.
Non-Final Office Action dated May 5, 2017, issued by the USTPO in U.S. Appl. No. 13/737,255.
Office Action dated May 2, 2017, issued by the Russian Patent Office in counterpart Application No.: 2013100165, which corresponds to U.S. Appl. No. 13/737,255.

* cited by examiner

SEM image of potassium guaiacolsulfonate particles
(magnification of lens: ×8000)

SEM image of potassium guaiacolsulfonate particles A
(magnification of lens: ×10000)

SEM image of potassium guaiacolsulfonate particles B
(magnification of lens: ×500)

SEM image of potassium guaiacolsulfonate particles C
(magnification of lens: ×500)

SEM image of glutathione (reduced form) particles
(magnification of lens: × 4000)

SEM image of aminophylline particles
(magnification of lens: × 3000)

Microscope image of Example 1
(magnification of lens: × 1000)

Microscope image of Example 2
(magnification of lens: × 1000)

Microscope image of Example 3
(magnification of lens: × 1000)

Microscope image of Example 4
(magnification of lens: × 1000)

Microscope image of Example 5
(magnification of lens: ×1000)

Microscope image of Example 6
(magnification of lens: ×1000)

Microscope image of Example 7
(magnification of lens: ×1000)

Microscope image of Example 8
(magnification of lens: × 1000)

Microscope image of Example 9
(magnification of lens: × 300)

Microscope image of Example 10
(magnification of lens: × 100)

Microscope image of Example 11
(magnification of lens: ×1000)

Microscope image of Example 12
(magnification of lens: ×1000)

Microscope image of Example 13
(magnification of lens: ×1000)

Microscope image of Comparative Example 1
(magnification of lens: × 1000)

Microscope image of Comparative Example 2
(magnification of lens: × 1000)

Microscope image of Comparative Example 3
(magnification of lens: × 1000)

Microscope image of Comparative Example 4 (magnification of lens: ×1000)

Microscope image of Comparative Example 5 (magnification of lens: ×1000)

Microscope image of Comparative Example 6 (magnification of lens: ×1000)

Microscope image of Comparative Example 7
(magnification of lens: × 1000)

FILM-FORM PREPARATION AND METHOD FOR PRODUCING THE SAME

TECHNICAL FIELD

The present invention relates to a film-form preparation (film-form medication) that readily dissolves in the mouth. More specifically, the present invention relates to a film-form preparation wherein drug particles for oral administration are dispersed such that the drug will dissolve rapidly in the mouth and be absorbed via the gastrointestinal tract or oral mucosa, and a method for producing the same.

BACKGROUND ART

At present orally administered drugs are marketed as uncoated tablets, coated tablets, capsules, powders, granules, liquids, etc.

Orally disintegrating tablets and rapidly dissolving oral films are already on the market as medications that disintegrate in the mouth and are absorbed by the gastrointestinal tract. Among these a film-form preparation is useful from the standpoint of rapid dissolution.

A considerable amount of research has been conducted on such film-form preparations. For example, Patent Document 1 discloses a film-form preparation comprising hydroxypropyl cellulose or a mixture of hydroxypropyl cellulose and polyvinyl pyrrolidone, a tannin, and a drug.

Patent Document 2 discloses a film-form preparation comprising a drug and low-substituted hydroxypropyl cellulose.

Patent Document 3 discloses a film-form preparation comprising a drug and hydroxypropyl cellulose.

Patent Document 4 discloses a film-form preparation comprising a drug and hydroxypropyl cellulose.

Patent Document 5 discloses a tablet obtained by drying a liquid suspension wherein a drug and polyvinyl pyrrolidone are dissolved or dispersed in an organic solvent.

Patent Document 6 discloses that a film-form preparation containing a drug can also contain polymers that are water-soluble, water-swellable, water-insoluble, or a combination thereof.

Patent Document 7 discloses a film-form preparation containing drug particles.

However, the appearance and physical properties such as feel, etc., of film-form preparations are still unsatisfactory because the drugs contained in prior art film-form preparations exist almost entirely in a dissolved state or, even if they are in a solid state, they have been dissolved and recrystallized in the preparation to obtain the solid state. Even in film-form preparations wherein the drug is present in a solid state, it has been almost impossible to contain the drug therein in a particulate state, let alone control the particle size, because the drug is dissolved at least once during the manufacturing process.

PRIOR ART DOCUMENT

Patent Document

Patent Document 1: JP-B 3496727
Patent Document 2: JP-A 2008-169138
Patent Document 3: JP-A 2004-43450
Patent Document 4: JP-T 2007-528876
Patent Document 5: JP-A H11-116465
Patent Document 6: WO 2004/066986
Patent Document 7: JP-T 2002-523359

SUMMARY OF THE INVENTION

Problems to be Solved by the Invention

In light of the above, an object of the present invention is to provide a film-form preparation with a rapid dissolution profile in the mouth and sufficient film strength, and with excellent appearance and feel, and a method for producing the same.

Means for Solving the Problems

After thorough and incisive investigation of the above problem, the inventors discovered that a film-form preparation with a rapid dissolution profile in the mouth and sufficient film strength, and with excellent appearance and feel can be obtained by preparing a film-form preparation including drug particles using a solvent in which the drug particles are insoluble and selecting an edible polymer which is soluble in the solvent, thus completing the present invention.

More specifically, the present invention is a film-form preparation including: a water-soluble and polar organic solvent-soluble edible polymer; and polar organic solvent-insoluble drug particles.

In addition, a particle size of the drug particles in the film-form preparation of the present invention is preferably 0.1 to 60 μm.

In addition, the edible polymer is preferably a solid at normal temperatures.

In addition, the edible polymer is preferably polyvinyl pyrrolidone, and/or hydroxypropyl cellulose.

In addition, a weight-average molecular weight of the polyvinyl pyrrolidone preferably ranges from 2,500 to 3,000,000.

In addition, a weight-average molecular weight of the hydroxypropyl cellulose preferably ranges from 10,000 to 1,150,000.

In addition, the hydroxypropyl cellulose preferably has a hydroxypropoxy group-substitution degree of 50 to 100%.

In addition, a solubility parameter of the polar organic solvent is preferably not less than 9.7.

The present invention is also a method for producing a film-form preparation including a water-soluble and polar organic solvent-soluble edible polymer and polar organic solvent-insoluble drug particles, and the method comprising: preparing a liquid dispersion of a drug containing the edible polymer, the drug particles, and a polar organic solvent; forming the liquid dispersion of the drug into a thin layer; and drying the thin layer.

The present invention is described in greater detail below.

The film-form preparation of the present invention contains an edible polymer that is soluble in water and also in a polar organic solvent, and drug particles that are insoluble in a polar organic solvent.

In this description, when an amount of less than 5 mL of a polar organic solvent is necessary to dissolve 1 g of solute at 20° C., then the solute is "water-soluble and polar organic solvent-soluble". When an amount of 100 mL or more of a polar organic solvent and water is necessary to dissolve 1 g of solute at 20° C., then the solute is "polar organic solvent-insoluble". When an amount of less than 3 mL of a polar organic solvent or water is necessary, then the solute is "easily soluble".

FIG. 1 is a schematic drawing showing one example of an embodiment of the film-form preparation of the present invention. As shown in FIG. 1, organic solvent-insoluble drug particles 1a are dispersed in a base material 1b containing the water-soluble and polar organic solvent-soluble edible polymer.

The drug particles can be localized to the surface of the base material or to a specific place therein, but preferably they are dispersed uniformly throughout the base material. Dispersing the drug particles uniformly in the base material enables rapid release of the drug in the mouth and improves the physical properties of the film-form preparation. Therefore, in the film-form preparation of the present invention the desired drug release properties for the drug particles can be attained without the need to coat the drug particles (e.g., encapsulate the drug particles in microcapsules).

The thickness of the film-form preparation of the present invention is not particularly limited herein, but a range of 30 to 300 µm, for example, is preferred. If the thickness is less than 30 µm, problems can arise from the standpoint of film strength of the film-form preparation and product handling properties; if the thickness exceeds 300 µm, the film-form preparation will require more time to dissolve in the mouth, and may not dissolve easily.

The planar shape of the film-form preparation of the present invention is not particularly limited herein, and it can be made into a desired shape such as a rectangle, square, circle, etc.

The drug particles used in the present invention have the solubility property of being insoluble in a polar organic solvent.

In the film-form preparation of the present invention, drug particles having the above solubility property are used as the drug particles, whereas a water-soluble and polar organic solvent-soluble polymer described below is used as the edible polymer wherein the drug particles are dispersed. Using a combination of the drug particles and the edible polymer with such solubility properties and using a polar organic solvent as the liquid medium during manufacture can facilitate containing the drug particles in a particulate state within the film-form preparation of the present invention and controlling the particle size thereof. By following the criteria below, for example, a person skilled in the art can easily and clearly discern the difference between drug particles in a recrystallized state and drug particles in a particulate state in a film-form preparation.

In other words, drug particles contained in a particulate state in a film-form preparation have irregular and nonuniform shapes and sizes, and are sometimes referred to as amorphous because they are organized spontaneously within the film-form preparation. Conversely, drug particles contained in a recrystallized state in a film-form preparation have an artificially manipulated shape and size because the manufacturer controls the particle size during manufacture.

Preferably, the drug particles are a solid at normal temperatures. When they are a solid at normal temperatures, the drug particles in the film-form preparation of the present invention can easily form a particulate state. The term "solid at normal temperatures" means a lack of liquidity at 20° C.

The average particle size of the drug particles in the film-form preparation of the present invention is preferably 0.1 to 60 µm. When the average particle size is less than 0.1 µm, individual drug particles may agglomerate and the flexibility of the film-form preparation can become nonuniform in places. When the average particle size exceeds 60 µm, the flexibility can also become nonuniform in places if the particles are contained in a film-form preparation of practical thickness.

More preferably, the average particle size of the drug particles is 0.1 to 30 µm. Having the average particle size in this range enables the preparation of a film-form preparation with uniform strength and flexibility at a practical thickness.

Here the term average particle size refers to the average particle size of the equivalent circular diameters of 50% of the particles by volume. The term equivalent circular diameter refers to the equivalent circular diameter of the projected area. More specifically it is the diameter of a circle with an area equal to that of the projection of the particle at plane, and is also referred to as the Heywood diameter.

If the average particle size of the drug particles lies outside the above range, sized particles falling within the above range can be used. Adjustment of the average particle size can be performed by pulverization, dry pulverization, granulation using wet granulation, etc., classification using a sieve, mechanical classifier, etc.

Preferably, the drug particles are prepared by granulating from the standpoint of physical properties and appearance of both the drug particles and the film-form preparation. Publicly known means, for example spray drying, jet milling, etc., can be noted as the technical means for granulating.

In addition, from the standpoint of physical properties and appearance of the film-form preparation, the drug particles do not need to be microencapsulated. Drug particles that are not microencapsulated are preferable from the standpoint of rapid dissolution.

In the present invention, the term drug particle refers to a mass of solid drug.

Such drug particles are not particularly limited in the present invention provided they have the above solubility properties of being insoluble in a polar organic solvent and can be administered orally. Concrete examples of such drugs include sedatives, expectorants, laxatives, anticancer drugs, antidiabetic drugs, anti-Parkinson's drugs, antidepressants, tranquilizers, anti-dementia drugs, antihypertensive drugs, anti-hyperlipidemia drugs, anti-migraine drugs, therapeutic agents for osteoporosis, therapeutic agents for hypotension, antitussive drugs, therapeutic agents for digestive ulcers, therapeutic agents for frequent urination and voiding disorders, therapeutic agents for urinary incontinence, anti-ulcer drugs, allergy drugs, 5-HT3 receptor antagonists (antiemetics), and the like.

Even more specifically, potassium guaiacolsulfonate particles, glutathione (reduced form) particles, aminophylline particles and the like can be noted as examples of the above drug particles.

Drug particles that do not taste bitter are preferred, but drug particles that do taste bitter can also be suitably used by performing a bitterness masking technique, for example, microencapsulation, or by adding a bitterness blocking agent, sweetener, flavoring, or fragrance.

The content of the drug particles will differ depending on the properties, etc., thereof, but preferably the content will be 0.1 to 80 wt % of the total content of solids contained in the film-form preparation of the present invention. When the content is less than 0.1 wt %, a rapid dissolution profile in the mouth and sufficient film strength may not be obtained. Moreover, a clear improvement over a film prepared by dissolving the drug may not be seen with regard to the gummy sensation in the mouth and sticky sensation when touched by the fingers resulting from the water-soluble polymer. However, this does not present a problem from a practical standpoint. On the other hand, when the content of drug particles exceeds 80 wt %, problems may occur in the shape retention properties, etc., of the product unless the particle size of the drug particles is made very small. A more preferred upper limit is 60 wt %. By making the content 60 wt % or less, the above advantageous effect of the present invention can be more properly obtained.

The edible polymer is a component constituting the base material of the film-form preparation of the present invention, and it is a polymer capable of being formed into a film.

The edible polymer is not particularly limited herein provided it is soluble in water and in a polar organic solvent and is edible, but preferably it is a solid at normal temperatures.

Preferably, such an edible polymer has a molecular weight of 2,000 to 4,000,000. When the molecular weight is less than 2,000, the film-forming properties will be poor, and retaining the shape of the film-form preparation may be difficult. On the other hand, when the molecular weight exceeds 4,000,000, the solubility of the film-form preparation will become poor, and this may become a problem from a practical standpoint. A more preferred molecular weight is a range of 2,500 to 3,000,000.

More specifically, the edible polymer to be used is preferably polyvinyl pyrrolidone (hereinafter, PVP), and/or hydroxypropyl cellulose (hereinafter, HPC).

These edible polymers exhibit sufficient solubility in water and polar organic solvents, and when used in a film-form preparation, they satisfy both the conditions of dissolving rapidly in the mouth and allowing use of organic solvents in which the drug particles are insoluble in the production. For this reason, drug particles insoluble in polar organic solvents can be uniformly dispersed and kept in a particulate state in base materials of the film-form preparation.

Among the above edible polymers, HPC is more preferred because HPC has less hygroscopicity with regard to relative humidity than PVP, and is considered preferable from a practical standpoint.

Preferably, the molecular weight of the above PVP is 2,500 to 3,000,000. When the molecular weight is less than 2,500, there is concern that stability, and hygroscopicity will be adversely affected; conversely, when the molecular weight exceeds 3,000,000, there is concern that solubility will become poor. A more preferred molecular weight is 2,500 to 1,200,000, and 2,500 to 1,000,000 is even more preferred.

In this description, the term the molecular weight refers to weight-average molecular weight, and is obtained by gel permeation chromatography analysis.

Preferably, the molecular weight of the above HPC is 10,000 to 1,150,000. When the molecular weight is less than 10,000, there is concern that hygroscopicity, and stability will be adversely affected, and when the molecular weight exceeds 1,150,000, there is concern that solubility will become poor. A more preferred molecular weight for the HPC is 10,000 to 370,000.

Preferably, the hydroxypropoxy group-substitution degree in the above HPC is 50 to 100%. When it is less than 50%, there is concern that the solubility thereof in water and polar organic solvents may become poor.

The method for measuring the hydroxypropoxy group-substitution degree follows the quantitative method described in the section entitled "Hydroxypropyl cellulose" in the Official Monographs of the Fifteenth Edition of the Japanese Pharmacopoeia. Preferably, the hydroxypropoxy group-substitution degree in the above HPC is at least 53.4%.

The film-form preparation of the present invention can use edible polymers which are soluble only in water or edible polymers which are insoluble both in water and polar organic solvents in proper combination therewith, other than the edible polymers described above.

Examples of the other edible polymer include synthetic polymers such as polyvinyl alcohol, carboxyvinyl polymer, hydroxypropyl methylcellulose, hydroxyethyl cellulose, methylcellulose, ethylcellulose, low-substituted hydroxypropyl cellulose, crystalline cellulose, carboxymethylcellulose sodium, carboxymethylcellulose calcium, carboxymethylcellulose, and carboxymethyl starch sodium; and polymers obtained from natural substances such as sodium alginate, dextran, casein, pullulan, pectin, guar gum, xanthan gum, tragacanth gum, acacia gum, gum arabic, and starch.

The content of the edible polymer in the film-form preparation of the present invention is preferably 1 to 80 wt % in relation to the total weight of solids contained therein. When the content of edible polymer is less than 1 wt %, the content of the aforementioned drug particles in the film-form preparation of the present invention will become too great, and unless the particle size of the drug particles is made very small, there will be a problem with shape retention properties, etc., of the product. On the other hand, when the content exceeds 80 wt %, a rapid dissolution profile in the mouth and sufficient film strength may not be obtained. The content is more preferably 10 to 70 wt %.

In addition to the above materials, the film-form preparation of the present invention can also contain a suitable amount of fragrance, flavoring, sweetener, coloring, preservative, antioxidant, stabilizer, surfactant, plasticizer (polyethylene glycol (PEG), etc.) within a range that does not hinder the effect of the present invention.

The film-form preparation of the present invention may contain particles of monosaccharide to hexasaccharide sugar and sugar alcohols thereof, if desired.

Since the drug particles in the film-form preparation of the present invention have not been dissolved, the sugar or sugar alcohols can be contained in a certain sized form. As a result, it is possible to reduce the risk of deteriorating physical properties and appearance of the film-form preparation and to add sweetness or moisture to the film-form preparation.

Examples of monosaccharides include: aldotetroses such as erythrose and threose; aldopentoses such as ribose, lyxose, xylose, and arabinose; aldohexoses such as allose, talose, gulose, glucose, altrose, mannose, galactose, and idose; ketotetroses such as erythrulose; ketopentoses such as xylulose and ribulose; and ketohexoses such as psicose, fructose, sorbose, and tagatose.

Examples of disaccharides include: α-diglucosides such as trehalose, kojibiose, nigerose, maltose, and isomaltose;

β-diglucosides such as isotrehalose, sophorose, laminaribiose, cellobiose, and gentiobiose; α,β-diglucocides such as neotrehalose; and lactose, sucrose, and isomaltulose (palatinose).

An example of a trisaccharide is raffinose, etc. Examples of tri- to hexasaccharide oligosaccharides include cyclic oligosaccharides such as fructooligosaccharides, galactooligosaccharides, xylooligosaccharides, isomaltooligosaccharides, chitin oligosaccharides, chitosan oligosaccharides, oligoglucosamine, and cyclodextrins, etc.

Examples of monosaccharide alcohols include: tetritols such as erythritol, D-threitol, and L-threitol; pentitols such as D-arabinitol and xylitol; hexitols such as D-iditol, galactitol (dulcitol), D-glucitol (sorbitol), and mannitol; and cyclitols such as inositol. Examples of disaccharide alcohols include maltitol, lactitol, and reduced palatinose (isomalt); and examples of oligosaccharides include pentaerythritol and reduced malt sugar starch syrup.

From the standpoint of ease of dissolution in the mouth of the film-form preparation of the present invention, monosaccharide to trisaccharide sugar and sugar alcohols thereof are preferably used. Further, lactose, erythritol, xylitol, mannitol, and reduced palatinose (isomalt) are more preferable because of their low hygroscopicity.

Preferable examples of the monosaccharide to hexasaccharide sugar and sugar alcohols thereof include those including particles with an average particle size of 0.1 to 60 μm. If the average particle size is less than 0.1 μm, the particles may aggregate one another so that the flexibility of the film-form preparation of the present invention may not be uniform in some parts. Conversely, if the average particle size exceeds 60 μm, similarly the flexibility may not be uniform in some parts, in a film-form preparation of practical thickness. The sugar and sugar alcohols more preferably have an average particle size of 0.1 to 30 μm.

Meanwhile, the average particle size of the sugar and sugar alcohols refers to a 50% by volume average particle size determined by a laser-scattering particle size distribution analyzer.

Namely, 10 mg of particles of the sugar or sugar alcohols are added in 3 mL of a chloroform solution of 0.2 wt % of polyoxyethylene monolauric acid ester, and the mixed solution is sufficiently dispersed by sonication. The dispersed solution is added to chloroform so that the transmittance becomes 75 to 85% in a laser-scattering particle size distribution analyzer (LA-950, product of Horiba Ltd.). Then, a 50% by volume average particle size is measured by the wet method.

The above sugars or sugar alcohol particles preferably constitute 1 to 80 wt % of the total weight of the solid portion of film-form preparation of the present invention. In a film-form preparation of practical thickness, if the amount of the sugars or sugar alcohols is less than 1 wt %, sufficient improvement is not seen in the properties of dissolution profile in the mouth, film strength, sticky sensation derived from water-soluble polymers in the mouth, and feeling when touched by the fingers. The amount exceeding 80 wt % may deteriorate the shape retention properties and the like of the film-form preparation, unless the average particle size of the sugar and sugar alcohols is significantly reduced. The amount of the sugar and sugar alcohols is more preferably 10 to 60 wt %.

As the foregoing sugar and the sugar alcohols, a commercially available product provided for use in medical products is conveniently utilized. Also, a commercially available product can be used after sizing so that the average particle size lies within the above range. Adjustment of the above average particle size can be carried out by pulverization or granulation using dry granulation, wet granulation, etc., classification using a sieve, mechanical classifier, etc.

A preferred polar organic solvent is one wherein the above edible polymer will dissolve, but the above drug particles will not dissolve, and an organic solvent with a solubility parameter of 9.7, for example, or higher can be suitably used. Examples of organic solvents satisfying such a solubility parameter include methanol, ethanol, isopropanol, propylene glycol, methylene chloride, and acetone, and preferably ethanol. These organic solvents may be a single solvent or a mixed solvent consisting of two or more kinds thereof.

In the present description, the term "solubility parameter" (SP value) refers to the square root of the heat of evaporation (cal/cm$^3$) required for one mole by volume of the liquid to evaporate. Table 1 shows the solubility parameter of organic solvents which can be used in production of the film-form preparation of the present invention and solubility parameter value of water.

Meanwhile, the solubility parameter of the organic solvent which can be used in the present invention is preferably 9.7 to 20, and more preferably 9.7 to 15. In the case of the solubility parameter of less than 9.7, the edible polymers such as polyvinyl pyrrolidone and hydroxypropyl cellulose may not be dissolved.

In the case of the solubility parameter exceeding 20, the drug particles may dissolve depending on the kinds, which is not preferable for the purpose of the present invention.

TABLE 1

| Solvent | Solubility parameter (SP value) |
|---|---|
| Methanol | 14.5~14.8 |
| Ethanol | 12.7 |
| Isopropanol | 11.5 |
| Propylene glycol | 14.3 |
| Methylene chloride | 9.7 |
| Acetone | 10.0 |
| Water | 23.4 |

The film-form preparation of the present invention can be manufactured, for example, by the following method.

Namely, first the desired amounts of edible polymer and drug particles adjusted so that the particle size by pulverization, granulation, a classifier, and the like, are added to a polar organic solvent capable of dissolving the above edible polymers, such as ethanol, propanol, and acetone to prepare a liquid dispersion of the drug. Next, the film-form preparation of the present invention can be produced by spreading a suitable amount of the liquid dispersion of the drug on a release film to form a thin film thereon, and then drying the thin film. In addition, the dried thin film is cut to a desired size, and as needed, sealed and packaged to produce a product.

Such a method for producing the film-form preparation of the present invention also constitutes the present invention.

During the production process of the film-form preparation of the present invention, when preparing the liquid dispersion of the drug, if the drug particles are added after the full amount of edible polymer is dissolved in a polar organic solvent, it may become difficult to disperse the drug particles sufficiently due to the viscosity of the polymer solution. As a result, in the method for producing the film-form preparation of the present invention it is preferable to first disperse the drug particles in a polar organic solvent to prepare a liquid dispersion of the drug and then dissolve the edible polymer therein.

If bubbles form in the liquid during the preparation of the above liquid dispersion of the drug, it is preferable to let the dispersion stand overnight and perform degassing under vacuum. Furthermore, preferably the polar organic solvent is the only medium used in preparing the liquid dispersion of the drug, but very small amounts purified water can also be added.

Effects of the Invention

The film-form preparation of the present invention can stably contain a sufficient quantity of drug expressing a rapid dissolution profile in the mouth because the drug particles are dispersed in a particulate state, and can have sufficient film strength, a satisfactory sensation when touched by the fingers, appearance, and the like.

Furthermore, the production method for the film-form preparation of the present invention enables the drug particles to be dispersed and carried in a film-form preparation without the need to dissolve the drug in solution, and therefore a film-form preparation containing the drug in a particulate state can be produced efficiently, and the size and shape of the drug particles can be controlled thereby.

MODES FOR CARRYING OUT THE INVENTION

Figure 1:
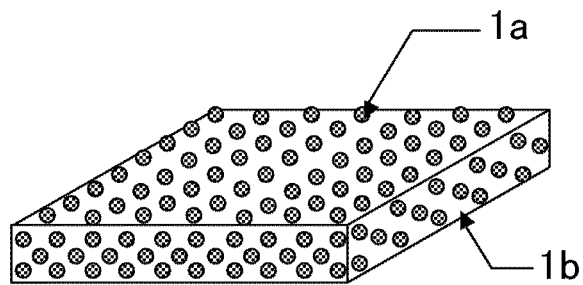
FIG. 1 is a schematic drawing showing one example of an embodiment of the film-form preparation of the present invention.

The present invention is described in detail through the following examples, but is by no means limited to those examples.

The various drug particles used in the Examples and Comparative Examples were obtained passing the powder through a 32 µm, 53 µm, 90 µm sieve after pulverization, or obtained fine particles by a jet mill (product of Hosokawa Micron Group, spiral jet mill model 50AS) or a spray dryer (product of Büchi Labortechnik AG, mini spray dryer model B-290) after pulverization. The particle sizes of these drug particles were measured by electron microscope (product of Hitachi High-Technologies Corp., model TM-1000) and the 50 vol % average particle size was calculated from the measurement results of 200 particles. This value was used as the particle size index of the particles.

Table 2 shows the 50 vol % average particle size and standard deviation of the drug particles. Images of these particles are shown in FIGS. 3 to 8.

TABLE 2

| Drug particles | 50 vol % average particle size [um] | Standard deviation [um] |
|---|---|---|
| Potassium guaiacolsulfonate particles | 5.0 | 1.4 |
| Potassium guaiacolsulfonate particles A | 2.1 | 0.3 |
| Potassium guaiacolsulfonate particles B | 40.4 | 9.4 |
| Potassium guaiacolsulfonate particles C | 80.4 | 25.8 |
| Glutathione (reduced form) particles | 5.3 | 0.9 |
| Aminophyllin particles | 4.3 | 0.9 |

Example 1

After 0.35 parts by weight of polyethylene glycol (PEG400) was added to 12.0 parts by weight of ethanol and stirred well, 6.65 parts by weight of HPC (product of Nippon Soda Co., Ltd., brand name: Nisso HPC SSL) with a molecular weight of approximately 30,000 and a hydroxypropoxy group-substitution degree of 53.4 to 77.5% was added, stirred, and dissolved using a rolling mixer. Then 3.0 parts by weight of previously sized potassium guaiacolsulfonate particles were added and dispersed by sonication to prepare a liquid dispersion of the drug. After the liquid dispersion of the drug was adequately degassed, it was spread onto a polyester release film and dried to prepare a film with a thickness of approximately 70 μm. The resulting film was peeled from the polyester release film and cut into 4 cm² rectangles to obtain the film-form preparation of Example 1.

Example 2

The film-form preparation of Example 2 was obtained using the same procedure as in Example 1 except PVP (product of Wako Pure Chemical Industries Co., Ltd., reagent name: polyvinyl pyrrolidone K90) with a molecular weight of 1,050,000 to 1,200,000 was used in place of the HPC to make the composition shown in Table 3.

Example 3

The film-form preparation of Example 3 was obtained using the same procedure as in Example 1 except that acetone was used in place of the ethanol to make the composition shown in Table 3.

Example 4

The film-form preparation of Example 4 was obtained using the same procedure as in Example 2 except that acetone was used in place of the ethanol to make the composition shown in Table 3.

Example 5

The film-form preparation of Example 5 was obtained using the same procedure as in Example 1 except previously sized glutathione (reduced form) particles were used in place of the potassium guaiacolsulfonate particles to make the composition shown in Table 3.

Example 6

The film-form preparation of Example 6 was obtained using the same procedure as in Example 1 except previously sized aminophylline particles were used in place of the potassium guaiacolsulfonate particles to make the composition shown in Table 3.

Example 7

The film-form preparation of Example 7 was obtained using the same procedure as in Example 6 except PVP (product of Wako Pure Chemical Industries Co., Ltd., reagent name: polyvinyl pyrrolidone K90) with a molecular weight of 1,050,000 to 1,200,000 was used in place of the HPC to make the composition shown in Table 3.

TABLE 3

| Component | Examples [Parts by weight] | | | | | | |
|---|---|---|---|---|---|---|---|
| | 1 | 2 | 3 | 4 | 5 | 6 | 7 |
| HPC | 6.65 | — | 6.65 | — | 6.65 | 6.65 | — |
| PVP | — | 6.65 | — | 6.65 | — | — | 6.65 |
| PEG400 | 0.35 | 0.35 | 0.35 | 0.35 | 0.35 | 0.35 | 0.35 |
| Potassium guaiacolsulfonate particles | 3.00 | 3.00 | 3.00 | 3.00 | — | — | — |
| Glutathione (reduced form) particles | — | — | — | — | 3.00 | — | — |
| Aminophyllin particles | — | — | — | — | — | 3.00 | 3.00 |
| Ethanol | 12.00 | 19.00 | — | — | 12.00 | 12.00 | 19.00 |
| Acetone | — | — | 12.00 | 19.00 | — | — | — |

Example 8

After 0.35 parts by weight of polyethylene glycol (PEG400) was added to 12.0 parts by weight of ethanol and stirred well, 6.65 parts by weight of HPC (product of Nippon Soda Co., Ltd., brand name: Nisso HPC SSL) with a molecular weight of approximately 30,000 and a hydroxypropoxy group-substitution degree of 53.4 to 77.5% was added, stirred, and dissolved using a rolling mixer. Then 3.0 parts by weight of previously sized potassium guaiacolsulfonate particles A were added and dispersed by sonication to prepare a liquid dispersion of the drug. After the liquid dispersion of the drug was adequately degassed, it was spread onto a polyester release film and dried to prepare a film with a thickness of approximately 70 μm. The resulting film was peeled from the polyester release film and was cut into 4 cm² rectangles to obtain the film-form preparation of Example 8.

Examples 9, 10

The film-form preparations of Example 9 and Example 10 were obtained using the same procedure as in Example 8 except previously sized potassium guaiacolsulfonate particles B and C were respectively used in place of the potassium guaiacolsulfonate particles A to make the compositions shown in Table 4.

Examples 11 to 13

The film-form preparations of Examples 11 to 13 were obtained using the same procedure as in Example 8 except for making the compositions shown in Table 4.

TABLE 4

| Component | Examples [Parts by weight] | | | | | |
|---|---|---|---|---|---|---|
| | 8 | 9 | 10 | 11 | 12 | 13 |
| HPC | 6.65 | 6.65 | 6.65 | 8.65 | 3.65 | 1.65 |
| PEG400 | 0.35 | 0.35 | 0.35 | 0.35 | 0.35 | 0.35 |
| Potassium guaiacolsulfonate particles A | 3.00 | — | — | 1.00 | 6.00 | 8.00 |
| Potassium guaiacolsulfonate particles B | — | 3.00 | — | — | — | — |
| Potassium guaiacolsulfonate particles C | — | — | 3.00 | — | — | — |
| Ethanol | 12.00 | 12.00 | 12.00 | 15.00 | 15.00 | 15.00 |

Comparative Example 1

First 0.35 parts by weight of polyethylene glycol (PEG400), 3.0 parts by weight of previously sized potassium guaiacolsulfonate particles, and 15.0 parts by weight of distilled water were added to 6.65 parts by weight of HPC (product of Nippon Soda Co., Ltd., brand name: Nisso HPC SSL) with a molecular weight of approximately 30,000 and a hydroxypropoxy group-substitution degree of 53.4 to 77.5%, and the mixture was stirred and dissolved using a rolling mixer. After the liquid dispersion of the drug was adequately degassed, it was spread onto a polyester release film and dried to prepare a film with a thickness of approximately 70 μm. The resulting film was peeled from the polyester release film and was cut into 4 cm² rectangles to obtain a film-form preparation of the Comparative Example 1.

Comparative Examples 2 to 4

The film-form preparations of Comparative Examples 2 to 4 were obtained using the same procedure as in Comparative Example 1 except PVP (product of Wako Pure Chemical Industries Co., Ltd., reagent name: polyvinyl pyrrolidone K90) with a molecular weight of 1,050,000 to 1,200,000 was used in Comparative Example 2, HPMC (product of Shin-etsu Chemical Co., Ltd., brand name: TC-5E) having a methoxy group-substitution degree of 28.0 to 30.0% and a hydroxypropoxy group-substitution degree of 7.0 to 12.0% with a weight average molecular weight of 16,000 was used in Comparative Example 3, and pullulan (product of Hayashibara Shoji INC., brand name: food additive pullulan) with a weight average molecular weight of 200,000 was used in Comparative Example 5, in place of the HPC to make the composition shown in Table 5.

Comparative Example 5

The film-form preparation of Comparative Example 5 was obtained using the same procedure as in Comparative Example 1 except previously sized glutathione (reduced form) particles were used in place of the potassium guaiacolsulfonate particles to make the composition shown in Table 5.

Comparative 6

The film-form preparation of Comparative Example 6 was obtained using the same procedure as in Comparative Example 1 except previously sized aminophylline particles were used in place of the potassium guaiacolsulfonate particles to make the composition shown in Table 5.

Comparative Example 7

The film-form preparation of Comparative Example 7 was obtained using the same procedure as in Comparative Example 6 except PVP (product of Wako Pure Chemical Industries Co., Ltd., reagent name: polyvinyl pyrrolidone K90) with a molecular weight of 1,050,000 to 1,200,000 were used in place of the HPC to make the composition shown in Table 5.

TABLE 5

| Component | Comparative Examples [parts by weight] | | | | | | |
|---|---|---|---|---|---|---|---|
| | 1 | 2 | 3 | 4 | 5 | 6 | 7 |
| HPC | 6.65 | — | — | — | 6.65 | 6.65 | — |
| PVP | — | 6.65 | — | — | — | — | 6.65 |
| HPMC | — | — | 6.65 | — | — | — | — |
| Pullulan | — | — | — | 6.65 | — | — | — |
| PEG400 | 0.35 | 0.35 | 0.35 | 0.35 | 0.35 | 0.35 | 0.35 |
| Potassium guaiacolsulfonate particles | 3.00 | 3.00 | 3.00 | 3.00 | — | — | — |
| Glutathione (reduced form) particles | — | — | — | — | 3.00 | — | — |
| Aminophyllin | — | — | — | — | — | 3.00 | 3.00 |
| Distilled water | 15.00 | 18.60 | 18.60 | 18.60 | 15.00 | 15.00 | 18.60 |
| Ethanol | — | — | — | — | — | — | — |

[Test Methods]

Measurements and evaluations were carried out on the film-form preparations prepared in these Examples and Comparative Examples for release properties during production, film flexibility, film strength, gummy sensation in the mouth, dissolution profile in the mouth, feel when touched by the fingers, and appearance by peeling test, stiffness test, tensile strength test, tack duration test, oral dissolution test, sensory test (feel), and visual observation. Images of the drug particles dispersed in the film-form preparation or drug crystals deposited in the film-form preparation were taken with a microscope. Each test method is described below.

(1) Release Properties Test

Samples were peeled from the polyester release films during production of each of the film-form preparations. The release properties were evaluated in the process. The evaluation criteria were as follows.
4: Can be peeled off easily
3: Can be peeled off
2: Can be peeled off with some effort
1: Can be peeled off with effort, but film tears
0: Cannot be peeled off at all (2) Stiffness Test This test was performed following the test method of "JIS L1096 Testing Methods for Woven Fabrics, 8.19 Stiffness, 8.19.1 Method A (45° cantilever method). In this test five 20 mm×150 mm test pieces were selected, and the short dimension of the test piece was aligned with the baseline of the scale on a smooth-surfaced, flat platform with one end having a 45° downward slope. Next, the test piece was gently slid in the direction of the slope by a suitable method, and when the center point of an edge of the test piece came into contact with the slope A, the position of the trailing edge was read on the scale. Stiffness is expressed as the length (mm) that the test piece was moved. Stiffness was determined by measuring the five test pieces both top up and bottom up, and both forward and backward, and then calculating the mean value.

For the evaluation reference values, evaluation films minus the drug particles were prepared for each film-form preparation in the Examples and Comparative Examples (Reference Examples 1 to 6 below). The stiffness of the film in each Reference Example was considered a reference value, and the following scale was established.
4: Reference value ±10 mm
3: Reference value ±20 mm
2: Reference value ±30 mm
1: Reference value ±40 mm or more The samples evaluated as being unable to be peeled off at all in the above (1) release properties test were given a score of 0 because they could not be examined.

Reference Example 1

First 0.5 parts by weight of polyethylene glycol (PEG400) and 15.0 parts by weight ethanol (99.5%) were added to 9.5 parts by weight of HPC (product of Nippon Soda Co., Ltd., brand name: Nisso HPC SSL) with a molecular weight of approximately 30,000 and a hydroxypropoxy group-substitution degree of 53.4 to 77.5%, and stirred and dissolved using a rolling mixer. After the solution was adequately degassed, it was spread onto a polyester release film and dried to prepare a film with a thickness of approximately 70 μm. The resulting film was peeled off from the polyester release film and cut into 4 cm² rectangles to obtain Evaluation Film (1).

Reference Examples 2 to 6

Evaluation Films (2) to (6) were obtained by the same procedure as in Reference Example 1 except the compositions shown in Table 6 were used. The PVP, HPMC and pullulan in Table 6 are the same as those described above.

TABLE 6

| | Reference Examples [parts by weight] | | | | | |
|---|---|---|---|---|---|---|
| Component | 1 | 2 | 3 | 4 | 5 | 6 |
| HPC | 9.5 | — | 9.5 | — | — | — |
| PVP | — | 9.5 | — | 9.5 | — | — |
| HPMC | — | — | — | — | 9.5 | — |
| Pullulan | — | — | — | — | — | 9.5 |
| PEG400 | 0.5 | 0.5 | 0.5 | 0.5 | 0.5 | 0.5 |
| Ethanol | 15.0 | 23.3 | — | — | — | — |
| Distilled water | — | — | 18.6 | 23.3 | 23.3 | 23.3 |
| Evaluation film | (1) | (2) | (3) | (4) | (5) | (6) |

(3) Tensile Strength Test

A small, tabletop, vertical tensile test apparatus (produced by Shimadzu Corporation, EZ TEST-100M) was used following "JIS K7127 Testing Method for Tensile Properties of Plastic Films and Sheets." The film-form preparation was cut to a 12 mm×50 mm test sample, and the test was performed after thorough drying in a desiccator. A rate of 60 mm/min was used as the draw rate. Because almost no stretching was seen in the test samples, the tensile strength at the measured yield point was used as the tensile strength value.

The test was repeated 3 times for each sample, and the mean value was recorded as the tensile strength. The tensile strength was then given a score using the following criteria.
4: 10 to 20 N
3: 5 to 10 N
2: 2 to 5 N
1: 0 to 2 N The samples evaluated as being unable to be peeled off at all in the above (1) release properties test were given a score of 0 because they could not be examined.

(4) Tack Duration Test

Figure 2:
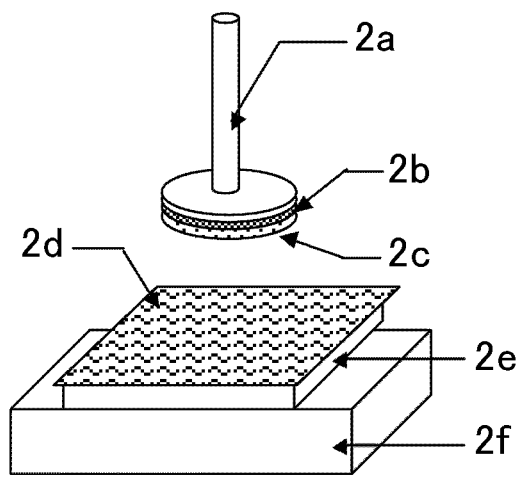
FIG. 2 is a schematic drawing showing the tack duration test.
Figure 3:
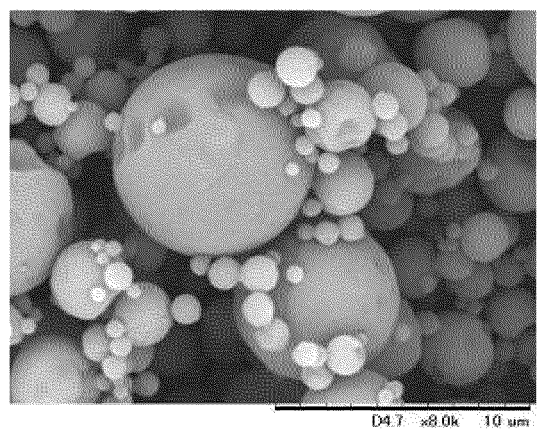
FIG. 3 is an SEM image of potassium guaiacolsulfonate particles.
Figure 4:
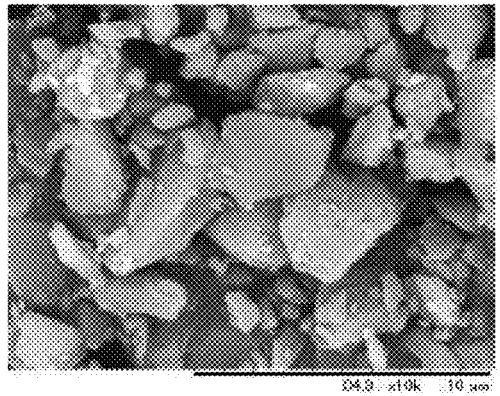
FIG. 4 is an SEM image of potassium guaiacolsulfonate particles A.
Figure 5:
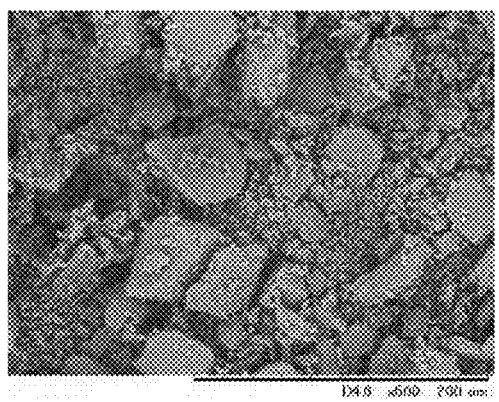
FIG. 5 is an SEM image of potassium guaiacolsulfonate particles B.
Figure 6:
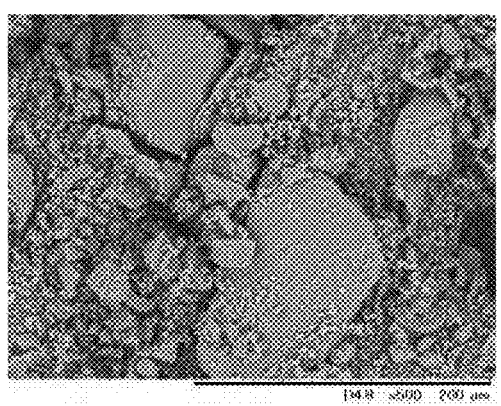
FIG. 6 is an SEM image of potassium guaiacolsulfonate particles C.
Figure 7:
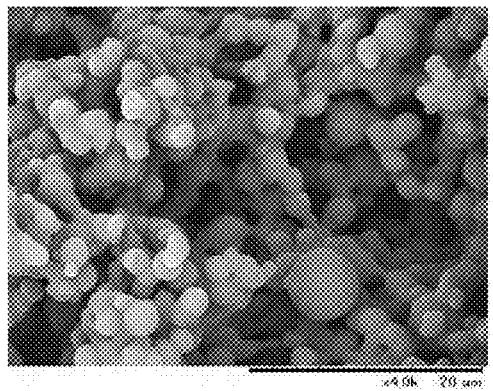
FIG. 7 is an SEM image of glutathione (reduced form) particles.
Figure 8:
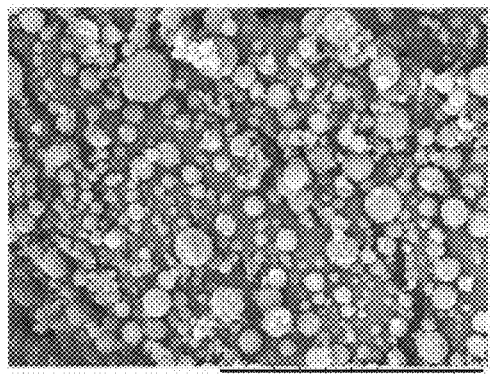
FIG. 8 is an SEM image of aminophylline particles.
Figure 9:
FIG. 9 is a micrograph of the surface of the film-form preparation of Example 1.
Figure 10:
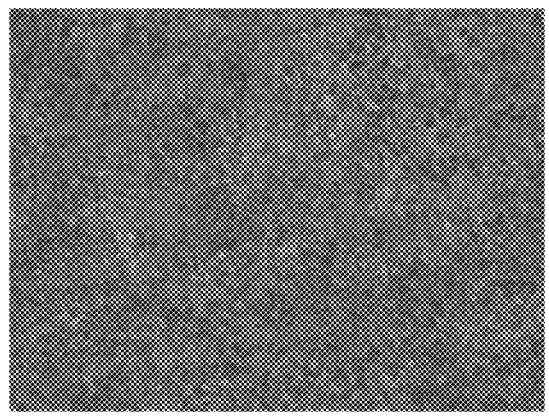
FIG. 10 is a micrograph of the surface of the film-form preparation of Example 2.
Figure 11:
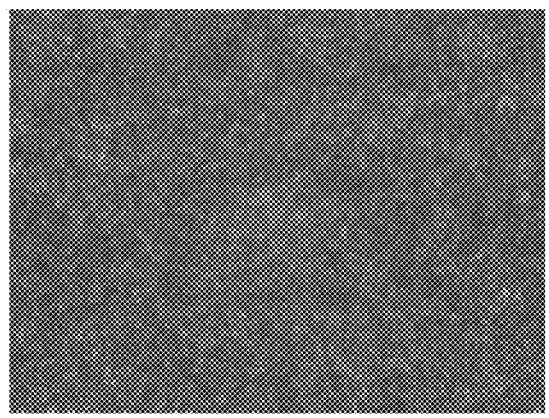
FIG. 11 is a micrograph of the surface of the film-form preparation of Example 3.
Figure 12:
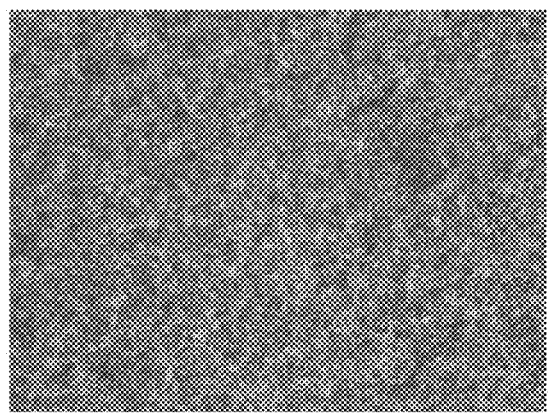
FIG. 12 is a micrograph of the surface of the film-form preparation of Example 4.
Figure 13:
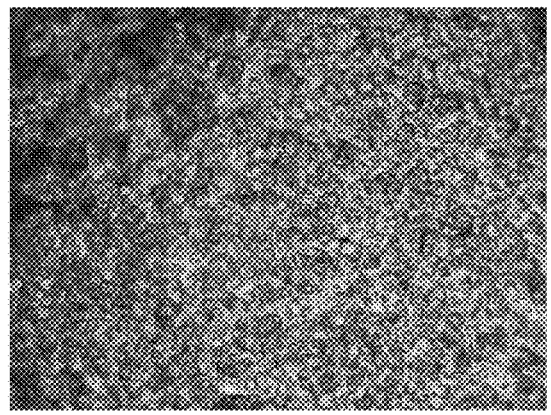
FIG. 13 is a micrograph of the surface of the film-form preparation of Example 5.
Figure 14:
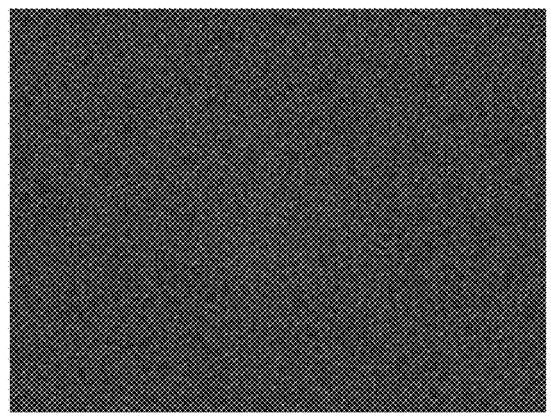
FIG. 14 is a micrograph of the surface of the film-form preparation of Example 6.
Figure 15:
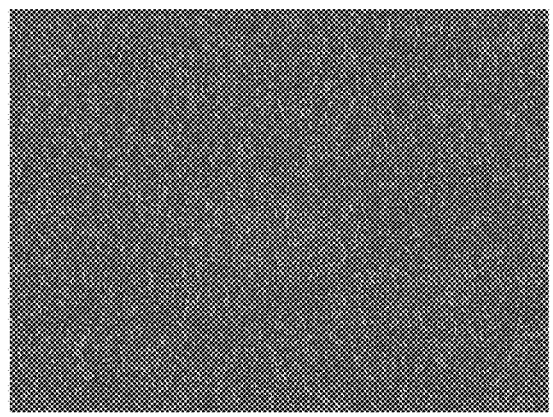
FIG. 15 is a micrograph of the surface of the film-form preparation of Example 7.
Figure 16:
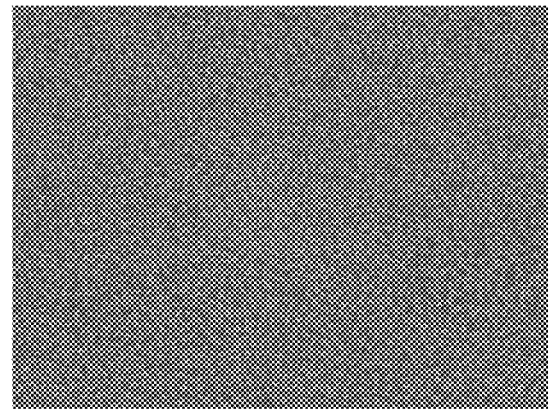
FIG. 16 is a micrograph of the surface of the film-form preparation of Example 8.
Figure 17:
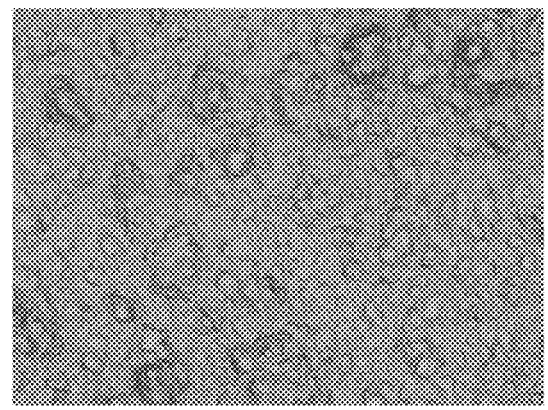
FIG. 17 is a micrograph of the surface of the film-form preparation of Example 9.
Figure 18:
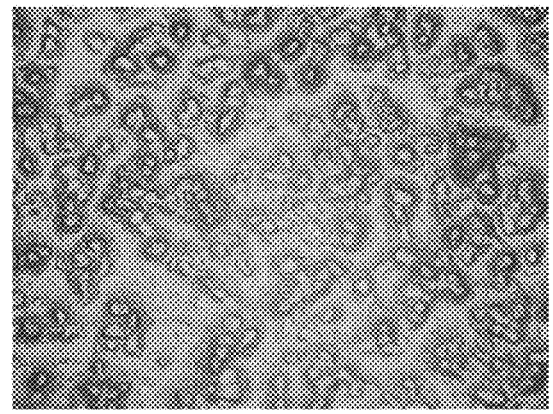
FIG. 18 is a micrograph of the surface of the film-form preparation of Example 10.
Figure 19:
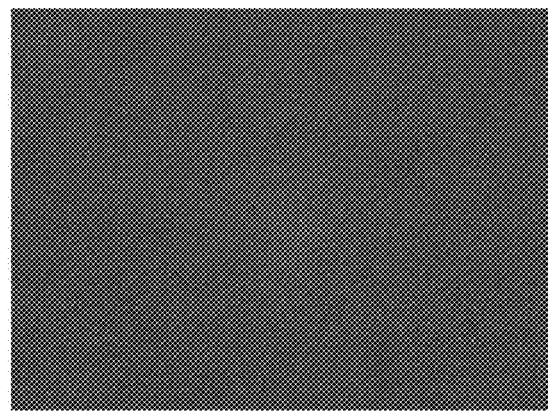
FIG. 19 is a micrograph of the surface of the film-form preparation of Example 11.
Figure 20:
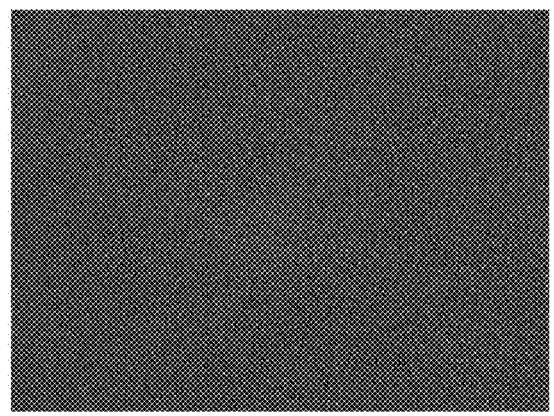
FIG. 20 is a micrograph of the surface of the film-form preparation of Example 12.
Figure 21:
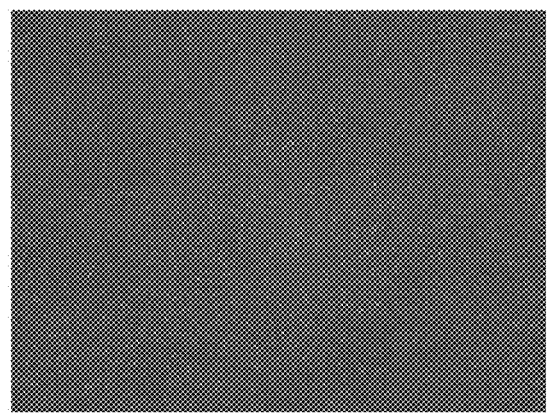
FIG. 21 is a micrograph of the surface of the film-form preparation of Example 13.
Figure 22:
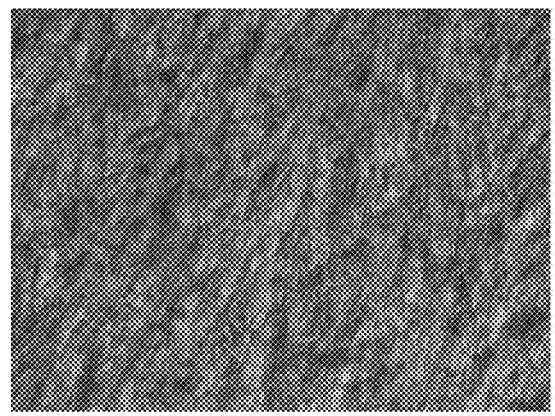
FIG. 22 is a micrograph of the surface of the film-form preparation of Comparative Example 1.
Figure 23:
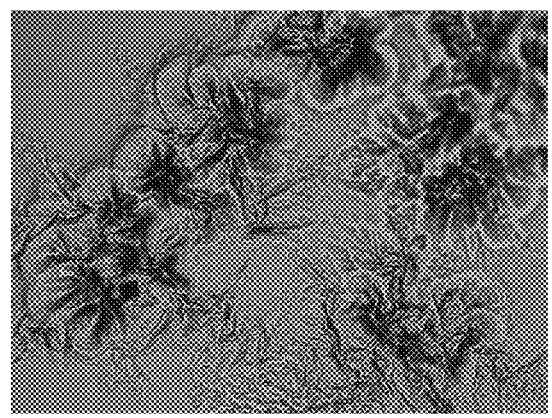
FIG. 23 is a micrograph of the surface of the film-form preparation of Comparative Example 2.
Figure 24:
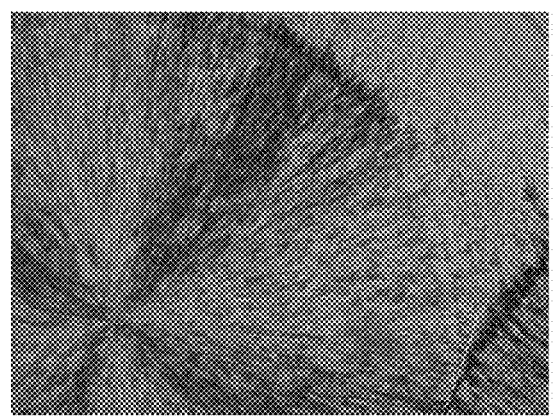
FIG. 24 is a micrograph of the surface of the film-form preparation of Comparative Example 3.
Figure 25:
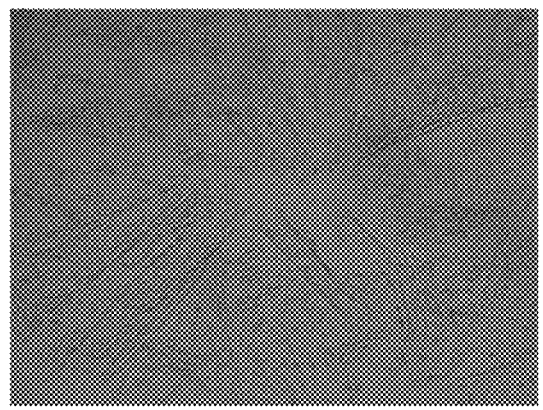
FIG. 25 is a micrograph of the surface of the film-form preparation of Comparative Example 4.
Figure 26:
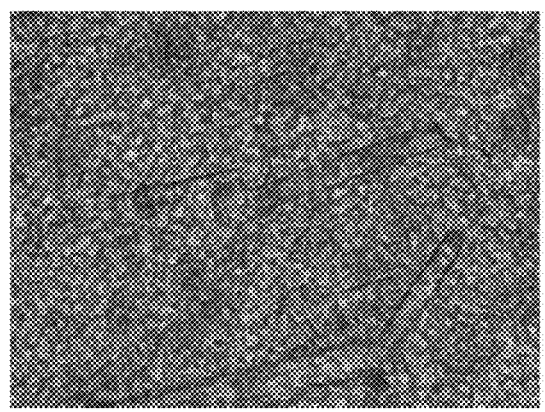
FIG. 26 is a micrograph of the surface of the film-form preparation of Comparative Example 5.
Figure 27:
FIG. 27 is a micrograph of the surface of the film-form preparation of Comparative Example 6.
Figure 28:
FIG. 28 is a micrograph of the surface of the film-form preparation of Comparative Example 7.

The test was performed under the environment shown in FIG. 2 using a rheometer (SUN SCIENTIFIC, CR-2000). First, a 12 mm diameter test piece 2c was adhered to a 12 mm diameter probe 2a with double-sided tape 2b. Separately, a piece of rubber 2e was mounted on the test platform 2f, and a collagen film 2d soaked with water was placed thereon. Then 200 μL of purified water was applied to the test piece, the probe 2a with the test piece 2c adhered thereto was lowered, placed in contact with the top of the collagen film 2d, and then raised. At that time, the tack duration after the initial tack, which was obtained when the probe 2a released from the collagen film 2d, was measured using slide caliper from recording paper. The criteria were as follows.
4: 0 to 10 mm
3: 10 to 15 mm
2: 15 to 20 mm
1: 20 mm or more The samples evaluated as being unable to be peeled off at all in the above (1) release properties test were cut together with the release film, and the release film side was adhered to the probe with double-sided tape. Then, the tack duration was measured in the same manner.

(5) Oral Dissolution Test

First 900 mL of pH 6.8 phosphate buffer was placed in a 1000 mL low glass petri dish, a stainless steel mesh basket (ϕ 4 mm) was inverted and submerged therein, and agitation was provided by a stirrer (300 rpm). The temperature of the liquid was maintained at 37±2° C. using a constant temperature water circulator. A test piece (4 cm²) was submerged, and concurrently a 3 cm²×3 cm² stainless steel screen (5 mm mesh) was placed on top as a sinker. The duration from the time the test piece was submerged until the test piece had finished disintegrating was checked visually and measured with a stop watch.

The measurement of each sample was repeated 3 times, and the mean was used as the oral dissolution time. The oral dissolution time was then given a score using the following criteria.

4: 0 to 10 sec
3: 10 to 15 sec
2: 15 to 20 sec
1: 20 sec or longer

The samples evaluated as being unable to be peeled off at all in the above (1) release properties test were given a score of 0 because they could not be examined.

(6) Sensory Test (Feel)

The cut film-form preparations from the Examples and Comparative Examples were evaluated for the unpleasant sensation of a sticky sensation on the surface by actually tracing a circle thereon with the fingers for 5 sec. The criteria were as follows.

4: No sticky sensation
3: Slightly sticky but not unpleasant
2: Unpleasant sticky sensation
1: Very sticky, and film remains on the fingers.

(7) Appearance (Visual)

The cut film-form preparations from the Examples and Comparative Examples were evaluated visually for film uniformity. The criteria were as follows.

4: The film is uniform
3: Fine deposits of crystals or fine aggregates of particles are visible in some places
2: Large deposits of crystals or large aggregates of particles are visible in some places
1: Deposits of crystals or aggregates of particles are visible in the majority of places Images of the drug particles or deposited drug crystals in the film of the respective film-form preparations according to Comparative Examples 1 to 7 and Examples 1 to 13 were taken with a microscope (product of Keyence Corp., model VHX-600). Each of the results was shown in FIGS. 7 to 26.

Table 7 shows the results of the release properties test, stiffness test, tensile strength test, tack duration test, oral dissolution test, sensory test (feel), and appearance (visual observation) performed on the film-form preparations of Examples and Comparative Examples. Total score of these seven evaluation items was obtained, and the film-form preparations of Examples and Comparative Examples were relatively evaluated based on the total scores.

TABLE 7

|  |  | Release properties | Stiffness Results | Stiffness Evaluation film | Tensile strength | Tack duration | Oral dissolution | Sensory (feel) | Appearance (visual observation) | Total |
|---|---|---|---|---|---|---|---|---|---|---|
| Examples | 1 | 4 | 4 | (1) | 4 | 4 | 4 | 4 | 4 | 28 |
|  | 2 | 4 | 4 | (2) | 4 | 3 | 3 | 4 | 4 | 26 |
|  | 3 | 4 | 4 | (1) | 4 | 4 | 4 | 4 | 4 | 28 |
|  | 4 | 4 | 4 | (2) | 4 | 3 | 3 | 4 | 4 | 26 |
|  | 5 | 4 | 4 | (1) | 4 | 4 | 4 | 4 | 4 | 28 |
|  | 6 | 4 | 4 | (1) | 4 | 3 | 4 | 4 | 4 | 27 |
|  | 7 | 4 | 4 | (2) | 4 | 3 | 4 | 4 | 4 | 27 |
|  | 8 | 4 | 4 | (1) | 4 | 4 | 4 | 4 | 4 | 28 |
|  | 9 | 4 | 3 | (1) | 3 | 3 | 4 | 4 | 4 | 25 |
|  | 10 | 4 | 4 | (1) | 2 | 3 | 4 | 4 | 4 | 25 |
|  | 11 | 4 | 4 | (1) | 4 | 3 | 4 | 4 | 4 | 27 |
|  | 12 | 4 | 4 | (1) | 3 | 3 | 4 | 4 | 4 | 26 |
|  | 13 | 4 | 4 | (1) | 2 | 3 | 4 | 4 | 4 | 25 |
| Comparative Examples | 1 | 2 | 3 | (3) | 2 | 4 | 3 | 3 | 1 | 18 |
|  | 2 | 2 | 2 | (4) | 1 | 3 | 4 | 2 | 2 | 16 |
|  | 3 | 2 | 2 | (5) | 1 | 4 | 4 | 3 | 2 | 18 |
|  | 4 | 2 | 2 | (6) | 1 | 4 | 3 | 3 | 1 | 16 |
|  | 5 | 1 | 4 | (3) | 3 | 4 | 1 | 3 | 1 | 17 |
|  | 6 | 0 | 0 | (3) | 0 | 4 | 0 | 3 | 1 | 8 |
|  | 7 | 0 | 0 | (4) | 0 | 3 | 0 | 2 | 1 | 6 |

As shown in Table 7, all drug particles in the film-form preparations of the Examples were contained in a particulate state, and most of the drug particles existed with an ordered particle size in a range of 1 to 60 μm. The total evaluation scores ranged from 25 to 28.

Meanwhile, in the film-form preparations according to Comparative Examples, the drug particles were contained in a dissolved or recrystallized state. The total evaluation scores ranged from 6 to 18.

INDUSTRIAL APPLICABILITY

The film-form preparation of the present invention can stably contain a sufficient quantity of drug expressing a rapid dissolution profile in the mouth because the drug particles are dispersed in a particulate state, and can have sufficient film strength, a satisfactory sensation when touched by the fingers, film appearance, and the like.

Furthermore, the production method for the film-form preparation of the present invention enables the drug particles to be dispersed and carried in the film-form preparation without the need to dissolve the same in solution, and therefore a film-form preparation containing the drug in a particulate state can be produced efficiently, and the size and shape of the drug particles can be controlled thereby.

EXPLANATION OF SYMBOLS

1a Drug particles
1b Base material
2a Probe
2b Double-sided tape
2c Test piece
2d Collagen film 2e Rubber
2f Test platform

The invention claimed is:

1. A film-form preparation comprising:
a water-soluble and polar organic solvent-soluble edible polymer; and
polar organic solvent-insoluble drug particles,
wherein said polar organic solvent-insoluble drug particles are contained in a particulate state within the film-form preparation,
wherein a particle size of the drug particles is 0.1 to 60 µm, and
wherein the content of the drug particles is 0.1 to 60 wt % of the total content of solids contained in the film-form preparation.

2. The film-form preparation according to claim 1, wherein the edible polymer is a solid at normal temperatures.

3. The film-form preparation according to claim 1, wherein the edible polymer is polyvinyl pyrrolidone and/or hydroxypropyl cellulose.

4. The film-form preparation according to claim 3, wherein a molecular weight of the polyvinyl pyrrolidone ranges from 2,500 to 3,000,000.

5. The film-form preparation according to claim 3, wherein a molecular weight of the hydroxypropyl cellulose ranges from 10,000 to 1,150,000.

6. The film-form preparation according to claim 3, wherein the hydroxypropyl cellulose has a hydroxypropoxy group-substitution degree of 50 to 100%.

7. The film-form preparation according to claim 1, wherein a solubility parameter of the polar organic solvent is not less than 9.7.

8. A method for producing a film-form preparation including a water-soluble and polar organic solvent-soluble edible polymer and polar organic solvent-insoluble drug particles, and the method comprising:
preparing a liquid dispersion of a drug containing the edible polymer, the drug particles, and a polar organic solvent;
forming the liquid dispersion of the drug into a thin layer; and
drying the thin layer,
wherein the particle size of the drug particles is 0.1 to 60 µm.

* * * * *